(12) United States Patent
Johnson

(10) Patent No.: US 6,458,979 B1
(45) Date of Patent: Oct. 1, 2002

(54) POLYMERIZATION OF ETHYLENE

(75) Inventor: Lynda Kaye Johnson, Wilmington, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 09/556,204

(22) Filed: Apr. 24, 2000

Related U.S. Application Data

(60) Provisional application No. 60/131,552, filed on Apr. 29, 1999.

(51) Int. Cl.[7] .................. C07F 15/00; C07C 251/00
(52) U.S. Cl. ..................... 556/34; 556/36; 556/37; 564/272
(58) Field of Search .................. 556/34, 36, 37; 564/272

(56) References Cited

U.S. PATENT DOCUMENTS

| | | | |
|---|---|---|---|
| 4,416,686 A | 11/1983 | Martin | 71/105 |
| 5,866,663 A | 2/1999 | Brookhart et al. | 526/170 |
| 5,955,555 A | 9/1999 | Bennett | 526/133 |

FOREIGN PATENT DOCUMENTS

| | | | |
|---|---|---|---|
| WO | WO98/30612 | 7/1998 | C08F/10/06 |
| WO | WO98/38228 | 9/1998 | C08F/10/02 |
| WO | WO99/02472 | 1/1999 | C07C/2/32 |
| WO | WO99/12981 | 3/1999 | C08F/4/70 |

OTHER PUBLICATIONS

Roy, et al., Metal Complexes of Sulfur–Nitrogen Chelating Agents. Part 12. The Chemistry of Nickel(II), Palladium(II), Cobalt(II) and Copper(II) Complexes of $N_2S_2$ and $N_3S_2$ Donor Systems, *Transition Met. Chem.,* 9, 152–155, 1984.

M. Park, et al., Molecular Recognition: Schiff Base as Molecular Tweezers, *Mol. Cryst. Liq. Cryst. Sci. Technol.,* 337, 485–488, 1999.

I. Bertini, et al., Synthesis and Proton Magnetic Resonance Studies of Paramagnetic Nickel(II), Complexes Containing Benzaldimine Groups. II. Five–Coordinate Complexes, *Inorg. Chem.,* 9(4), 698–702, 1970.

E. Bouwman, et al., Synthesis of the ligand N,N'–bis(2–tert–butylthiobenzenylidene)–diethylnetriamine; its reactivity with nickel(II) salts, *Inorg. Chem. Acta,* 287(1), 105–108, 1999.

International Search Report dated Aug. 30, 2000 for PCT/US00/11047.

*Primary Examiner*—Porfirio Nazario-Gonzalez

(57) ABSTRACT

Polyethylene is formed by contacting ethylene with a novel iron or cobalt complex of a selected 1,4,7-triaza-3-oxa-1,4,6-heptatriene or 2,5,8-triaza-1,8-nonadiene, optionally in the presence of a cocatalyst such as an alkylaluminum compound. The polymers formed as useful for molding and in films.

6 Claims, No Drawings

POLYMERIZATION OF ETHYLENE

CROSS-REFERENCE TO RELATED APPLICATION

This application claims priority under 35 U.S.C. §119 from U.S. Provisional Application Ser. No. 60/131,552 (filed Apr. 29, 1999), which is incorporated by reference herein as if fully set forth.

FIELD OF THE INVENTION

Iron and cobalt complexes of selected 1,4,7-triaza-3-oxa-1,4,6-heptatrienes or 2,5,8-triaza-1,8-nonadienes are catalysts for the polymerization of ethylene, optionally in the presence of cocatalysts such as alkylaluminum compounds.

TECHNICAL BACKGROUND

Polyethylenes are very important items of commerce, large quantities of various grades of these polymers being produced annually for a large number of uses, such as packaging films and moldings. There are many different methods for making such polymers, including many used commercially, such as free radical polymerization to make low density polyethylene, and many so-called coordination catalysts such as Ziegler-Natta-type and metallocene-type catalysts. Each of these catalyst systems has its advantages and disadvantages, including cost of the polymerization and the particular structure of the polyethylene produced. Due to the importance of polyethylenes, new catalyst systems which are economical and/or produce new types of polyethylenes are constantly being sought.

U.S. Pat. No. 5,955,555, WO98/30612, WO98/38228, WO99/02472 and WO99/12981 (incorporated by reference herein for all purposes) describe the use of iron or cobalt complexes of 2,6-diacylpyridinebisimines or 2,6-pyridinedicarboxaldehydebisimines as catalysts for the polymerization of olefins, mostly of ethylene. These publications describe the preparation of polyethylenes ranging in molecular weight from low molecular weight alpha-olefins and other oligomers to high molecular weight polyethylenes. No mention is made, however, of the use of ligands such as described herein.

R. Roy, et al., *Transition Met. Chem.* (Weinheim, Ger.), vol. 9, p. 152–155 (1984) describes cobalt complexes of certain aminodiimines. No mention is made of ligands or metal complexes such as described herein.

SUMMARY OF THE INVENTION

This invention concerns a first process for the production of polyethylene, comprising the step of contacting, at a temperature of about −100° C. to about +200° C., a monomer component comprising ethylene, and an Fe or Co complex of a ligand of the formula

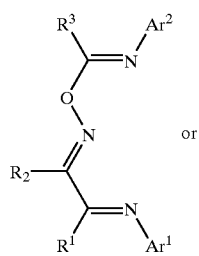

(I)

or

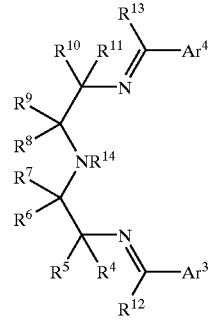

(III)

wherein:

$R^1$, $R^2$ and $R^3$ are each independently hydrogen, hydrocarbyl, substituted hydrocarbyl or a functional group, or $R^1$ and $R^2$ taken together may form a ring;

$Ar^1$ and $Ar^2$ are each independently aryl or substituted aryl;

$R^4$, $R^5$, $R^6$, $R^7$, $R^8$, $R^9$, $R^{10}$, $R^{11}$, $R^{12}$ and $R^{13}$ are each independently hydrogen, hydrocarbyl, substituted hydrocarbyl, or a functional group, provided that any two of $R^4$, $R^5$, $R^6$, $R^7$, $R^8$, $R^9$, $R^{10}$ and $R^{11}$ that are vicinal to one another may form a ring;

$R^{14}$ is hydrogen, hydrocarbyl or substituted hydrocarbyl; and $Ar^3$ and $Ar^4$ are each independently aryl or substituted aryl.

Also disclosed herein is a second process for the production of polyethylene, comprising the step of contacting, at a temperature of about −100° C. to about +200° C., a monomer component comprising ethylene, a compound of the formula

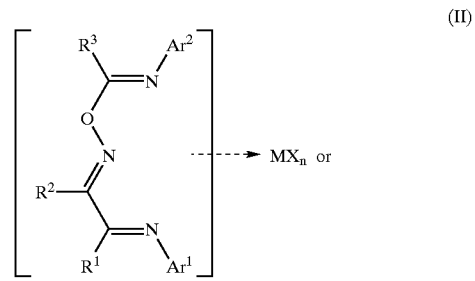

(II)

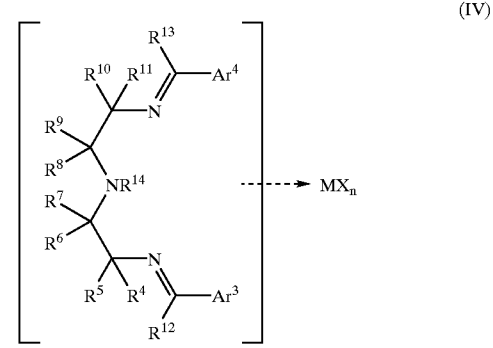

(IV)

and:

(a) a first compound W, which is a neutral Lewis acid capable of abstracting $X^-$, an alkyl group or a hydride group from M to form $WX^-$, $(WR^{20})^-$ or $WH^-$, and which is also capable of transferring an alkyl group or a hydride to M, provided that WX⁻ is a weakly coordinating anion; or (b) a combination of second compound which is capable of transferring an alkyl or hydride group to M and a third compound which is a neutral Lewis acid which is capable of abstracting X⁻, a hydride or an alkyl group from M to form a weakly coordinating anion;

wherein:

M is Fe or Co;

each X is an anion;

n is an integer so that the total number of negative charges on said anion or anions is equal to the oxidation state of M;

$R^1$, $R^2$ and $R^3$ are each independently hydrogen, hydrocarbyl, substituted hydrocarbyl or a functional group, or $R^1$ and $R^2$ taken together may form a ring;

$Ar^1$ and $Ar^2$ are each independently aryl or substituted aryl;

$R_4$, $R^5$, $R^6$, $R^7$, $R^8$, $R^9$, $R^{10}$, $R^{11}$, $R^{12}$ and $R^{13}$ are each independently hydrogen, hydrocarbyl, substituted hydrocarbyl, or a functional group, provided that any two of $R^4$, $R^5$, $R^6$, $R^7$, $R^8$, $R^9$, $R^{10}$ and $R^{11}$ that are vicinal to one another may form a ring;

$R^{14}$ is hydrogen, hydrocarbyl or substituted hydrocarbyl;

$Ar^3$ and $Ar^4$ are each independently aryl or substituted aryl; and $R^{20}$ is alkyl.

This invention also concerns a third process for the production of polyethylene, comprising the step of contacting, at a temperature of about −100° C. to about +200° C., a monomer component comprising ethylene, and a compound of the formula

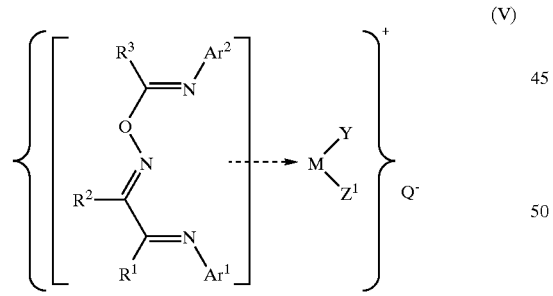

(V)

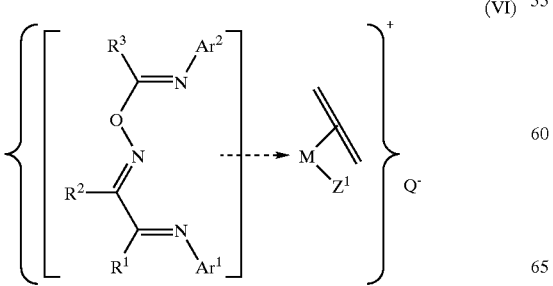

(VI)

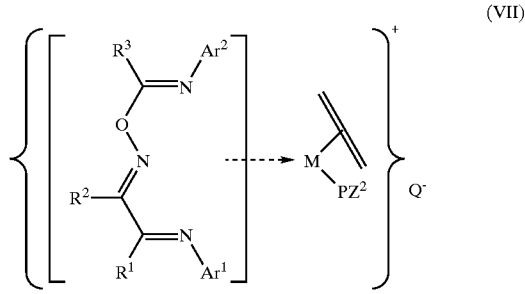

(VII)

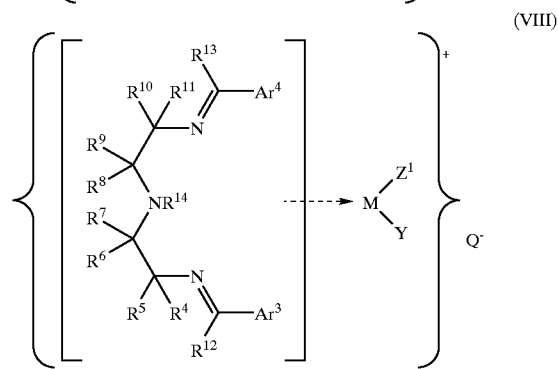

(VIII)

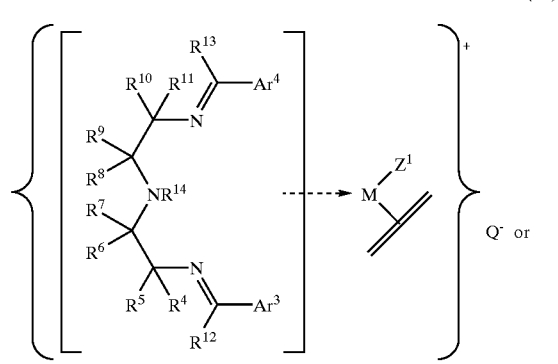

(IX)

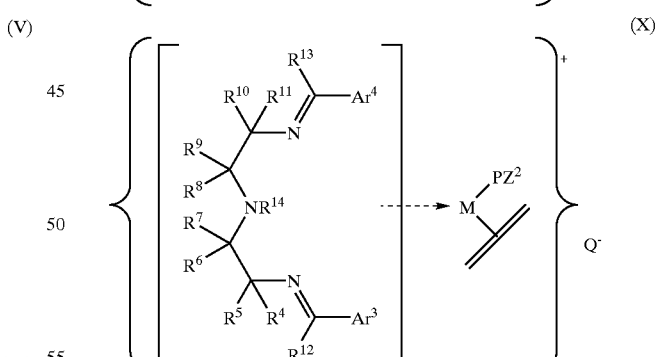

(X)

wherein:

M is Fe or Co;

$R^1$, $R^2$ and $R^3$ are each independently hydrogen, hydrocarbyl, substituted hydrocarbyl or a functional group, or $R^1$ and $R^2$ taken together may form a ring;

$Ar^1$ and $Ar^2$ are each independently aryl or substituted aryl;

$R^4$, $R^5$, $R^6$, $R^7$, $R^8$, $R^9$, $R^{10}$, $R^{11}$, $R^{12}$ and $R^{13}$ are each independently hydrogen, hydrocarbyl, substituted hydrocarbyl, or a functional group, provided that any two of $R^4$, $R^5$, $R^6$, $R^7$, $R^8$, $R^9$, $R^{10}$ and $R^{11}$ that are vicinal to one another may form a ring;

$R^{14}$ is hydrogen, hydrocarbyl or substituted hydrocarbyl;

$Ar^3$ and $Ar^4$ are each independently aryl or substituted aryl;

$Z^1$ is hydride, alkyl or an anionic ligand into which ethylene can insert;

Y is a neutral ligand capable of being displaced by ethylene, or a vacant coordination site;

Q is a relatively non-coordinating anion;

P is a divalent polyethylene group containing one or more ethylene units; and $Z^2$ is an end group.

Also disclosed herein is a compound of the formula

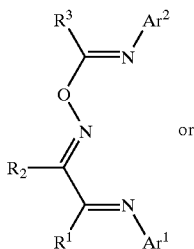

(I)

or

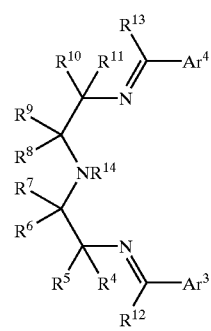

(III)

wherein:

$R^1$, $R^2$ and $R^3$ are each independently hydrogen, hydrocarbyl, substituted hydrocarbyl or a functional group, or $R^1$ and $R^2$ taken together may form a ring;

$Ar^1$ and $Ar^2$ are each independently aryl or substituted aryl;

$R^4$, $R^5$, $R^6$, $R^7$, $R^8$, $R^9$, $R^{10}$, $R^{11}$, $R^{12}$ and $R^{13}$ are each independently hydrogen, hydrocarbyl, substituted hydrocarbyl, or a functional group, provided that any two of $R^4$, $R^5$, $R^6$, $R^7$, $R^8$, $R^9$, $R^{10}$ and $R^{11}$ that are vicinal to one another may form a ring;

$R^{14}$ is hydrogen, hydrocarbyl or substituted hydrocarbyl; and $Ar^3$ and $Ar^4$ are each independently aryl or substituted aryl.

Another compound disclosed herein is a compound of the formula

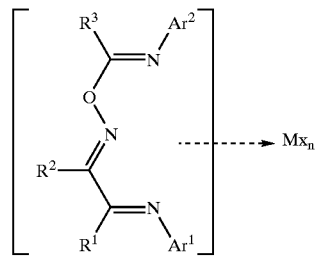

(II)

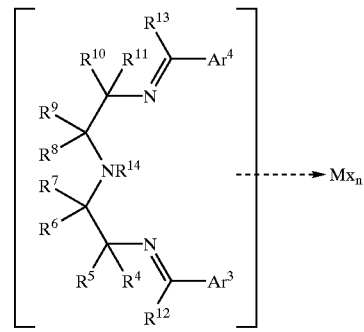

(IV)

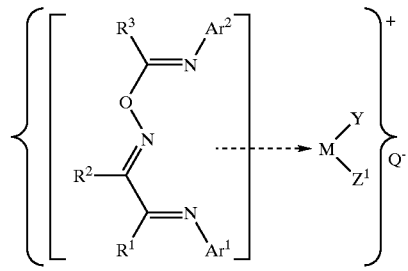

(V)

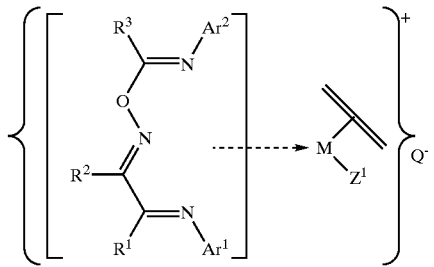

(VI)

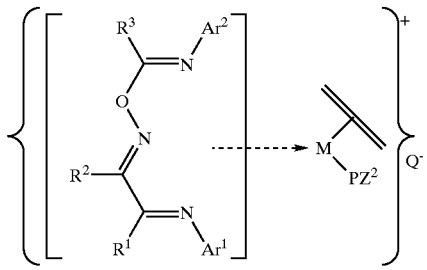

(VII)

-continued

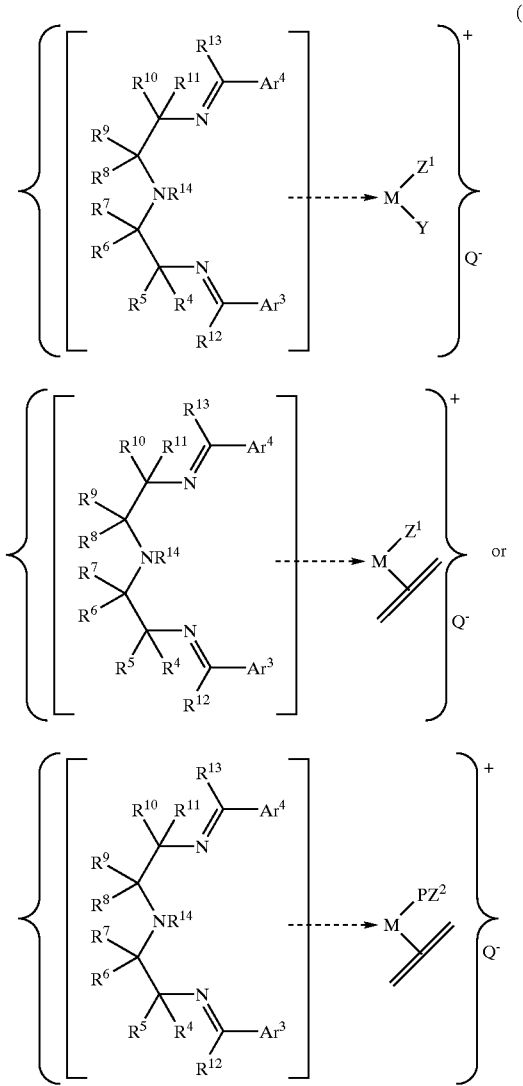

wherein:

M is Fe or Co;

$R^1$, $R^2$ and $R^3$ are each independently hydrogen, hydrocarbyl, substituted hydrocarbyl or a functional group, or $R^1$ and $R^2$ taken together may form a ring;

$Ar^1$ and $Ar^2$ are each independently aryl or substituted aryl;

$R^4$, $R^5$, $R^6$, $R^7$, $R^8$, $R^9$, $R^{10}$, $R^{11}$, $R^{12}$ and $R^{13}$ are each independently hydrogen, hydrocarbyl, substituted hydrocarbyl, or a functional group, provided that any two of $R^4$, $R^5$, $R^6$, $R^7$, $R^8$, $R^9$, $R^{10}$ and $R^{11}$ that are vicinal to one another may form a ring;

$R^{14}$ is hydrogen, hydrocarbyl or substituted hydrocarbyl;

$Ar^3$ and $Ar^4$ are each independently aryl or substituted aryl;

$Z^1$ is hydride or alkyl or any other anionic ligand into which ethylene can insert;

Y is a neutral ligand capable of being displaced by ethylene, or a vacant coordination site;

Q is a relatively non-coordinating anion;

P is a divalent polyethylene group containing one or more ethylene units; and $Z^2$ is an end group.

DETAILED DESCRIPTION OF THE PREFERRED EMBODIMENTS

A structure drawn such as (II), (IV) and (V) through (X) simply means that the ligand in the square bracket is coordinated to the metal-containing moiety, as indicated by the arrow. Nothing is implied in these formulas about what atoms in the ligand are coordinated to the metal. Without wishing to be bound by any particular theory, it is believed that (I) and (III) are tridentate ligands in coordinating with Fe or Co, and that coordination is effected through the nitrogen atoms shown in formulas (I) and (III).

Herein, certain terms are used. Some of them are:

A "hydrocarbyl group" is a univalent group containing only carbon and hydrogen. If not otherwise stated, it is preferred that hydrocarbyl groups herein contain 1 to about 30 carbon atoms.

By "substituted hydrocarbyl" herein is meant a hydrocarbyl group which contains one or more substituent groups which are inert under the process conditions to which the compound containing these groups is subjected. The substituent groups also do not substantially interfere with the process. If not otherwise stated, it is preferred that substituted hydrocarbyl groups herein contain 1 to about 30 carbon atoms. Included in the meaning of "substituted" are heteroaromatic rings. Also included in such groups are those in which hydrogen has been completely replaced by another group or element, as in trifluoromethyl.

By "(inert) functional group" herein is meant a group other than hydrocarbyl or substituted hydrocarbyl which is inert under the process conditions to which the compound containing the group is subjected. The functional groups also do not substantially interfere with (impede) any process described herein that the compound in which they are present may take part in. Examples of functional groups include, but are not limited to, halo (fluoro, chloro, bromo and iodo), ether such as $-OR^{18}$ wherein $R^{18}$ is hydrocarbyl or substituted hydrocarbyl, nitro, silyl, tertiary amino, thioether and ester. In cases in which the functional group may be near a cobalt or iron atom, the functional group should preferably not coordinate to the metal atom more strongly than the usual coordinating groups, that is they should preferably not displace the desired coordinating group.

By an "alkyl aluminum compound" is meant a compound in which at least one alkyl group is bound to an aluminum atom. Other groups such as alkoxide, hydride, and halogen may also be bound to aluminum atoms in the compound.

By "neutral Lewis base" is meant a compound, which is not an ion, which can act as a Lewis base. Examples of such compounds include ethers, amines, sulfides, and organic nitrites.

By "cationic Lewis acid" is meant a cation which can act as a Lewis acid. Examples of such cations are sodium and silver cations.

By "relatively noncoordinating anions" (or "weakly coordinating anions") is meant those anions as are generally referred to in the art in this manner, and the coordinating ability of such anions is known and has been discussed in the literature, see for instance W. Beck, et al., *Chem. Rev.*, vol. 88 p. 1405–1421 (1988), and S. H. Strauss, *Chem. Rev.*, vol. 93, p. 927–942 (1993), both of which are hereby included by reference. Among such anions are those formed from the aluminum compounds in the immediately preceding paragraph and $X^-$, including $R^9{}_3AlX^-$, $R^9{}_2AlClX^-$, $R^9AlCl_2X^-$, and "R$^9$AlOX$^-$", wherein R$^9$ is alkyl. Other useful noncoordinating anions include BAF$^-$ {BAF=tetrakis[3,5-bis(trifluoromethyl)phenyl]borate}, SbF$_6^-$, PF$_6^-$, and BF$_4^-$, trifluoromethanesulfonate, p-toluenesulfonate, (R$_f$SO$_2$)$_2$N$^-$, and (C$_6$F$_5$)$_4$B$^-$.

By an "empty coordination site" is meant a potential coordination site that is not occupied by a ligand. Thus if an ethylene molecule is in the proximity of the empty coordination site, the ethylene molecule may coordinate to the metal atom.

"Aryl" herein also includes heterocyclic rings.

By a "ligand that may add to ethylene" is meant a ligand coordinated to a metal atom into which an ethylene molecule (or a coordinated ethylene molecule) may insert to start or continue a polymerization. For instance, this may take the form of the reaction (wherein L is a ligand):

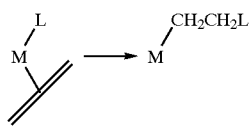

By a "1,4,7-triaza-3-oxa-1,4,6-heptatriene" herein is meant a compound having the backbone (with appropriate groups attached of

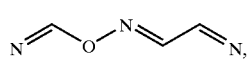

(XIII)

while by a "2,5,8-triaza-1,8-nonadiene" is meant a compound with the backbone (with appropriate groups attached) of

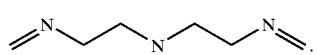

(XIV)

By an "end group" such as Z$^2$ is meant a group bound to the metal atom into which the first ethylene molecule of the polymer being formed inserted. Typically this will be Z$^1$.

By "=" in formulas such as (VI), (VII), (IX) and (X) is meant an ethylene molecule.

By "polyethylene" is, in its broadest sense, meant a polymer based predominantly on ethylene, that is, a polymer in which at least 50 mole percent of the repeat units are dervied from ethylene in the polymerization process.

Preferably, the polyethylenes referred to herein have at least 70 mole percent, and more preferably at least 80 mole percent, of the repeat units are derived from ethylene in the polymerization process. By a "homopolyethylene" herein is meant a polymer in which substantially all of the repeat units are derived from ethylene in the polymerization process. "Derived from ethylene" includes any comonomers generated in situ (either simultaneously with or in series with the actual polymerization) from ethylene such as, for example, those ethylene oligomers formed by the ethylene oligomerization catalyst. Homopolyethylenes are preferred herein.

Iron is a preferred transition metal in all coordination compounds of (I) and (III) (and in processes in which they are used) herein.

Preferred groups in compounds (I) and (III) and their corresponding metal complexes are:

R$^1$ and R$^2$ are each independently hydrogen or alkyl containing 1 to 4 carbon atoms, more preferably both R$^1$ and R$^2$ are hydrogen or methyl; and/or R$^1$ and R$^2$ taken together form a ring, more preferably a carbocyclic ring, and especially preferably R$^1$ and R$^2$ taken together are

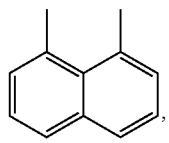

(XI)

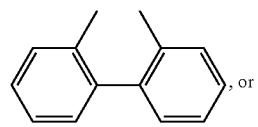

(XII)

, or

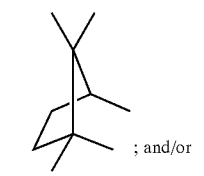

(XV)

; and/or

R$^3$ is aryl, substituted aryl or alkyl, more preferably aryl, substituted aryl or alkyl containing 1 to 4 carbon atoms, especially preferably phenyl, t-butyl or methyl; and/or Ar$^1$ and Ar$^2$ are 2-substituted (with no substitution in the 6 position) or 2,6-disubstituted phenyl with substitution optional at any other ring position; and more preferably the substituents in the 2 and 6 (when present) positions are alkyl containing 1 to 4 carbon atoms or hydrogen; and/or R$^4$, R$^5$, R$^6$, R$^7$, R$^8$, R$^9$, R$^{10}$, R$^{11}$, R$^{12}$ and R$^{13}$ are each 25 hydrogen; and/or R$^{12}$ and R$^{13}$ are hydrogen; and/or R$^{14}$ is hydrogen or hydrocarbyl, more preferably hydrogen or alkyl, especially preferably methyl or hydrogen, and highly preferably hydrogen; and/or Ar$^3$ and Ar$^4$ are 2-substituted (with no substitution in the 6 position) or 2,6-disubstituted phenyl with substitution optional at any other ring position; and more preferably the substituents in the 2 and 6 (when present) positions are alkyl containing 1 to 4 carbon atoms or hydrogen; and/or Ar$^3$ and Ar$^4$ are 9-anthracenyl; and/or Ar$^3$ and Ar$^4$ are the same.

In compounds in which it occurs, it is preferred that X is halo (especially chloride or bromide), carboxylate such as acetate, citrate, cyclohexane butyrate, 2-ethylhexanoate, stearate and oxalate, acetylacetonate, benzoylacetonate, hexafluoroacetylacetonate, hydroxide, 2,2,6,6-tetramethyl-3,5-heptanedionate, p-toluenesulfonate, ethoxide, i-propoxide, trifluoroacetylacetonate, and tetrafluoroborate. Especially preferred anions X are halide, carboxylate and acetylacetonate.

The iron and cobalt in the complexes may be in the +2 or +3 oxidation state, and +2 is preferred.

Ar$^1$, Ar$^2$, Ar$^3$, and Ar$^4$ may also each independently be aryl, substituted aryl, hydrocarbyl or substituted hydrocarbyl provided that in the hydrocarbyl or substituted hydrocarbyl groups the carbon atom bound to the imino nitrogen is bound to at least two other carbon atoms. It is preferred that Ar$^1$, Ar$^2$, Ar$^3$, and Ar$^4$ are each independently aryl or substituted aryl.

Specific preferred compounds for (I) and (III), and their corresponding Fe and Co complexes, are:

(Ia) 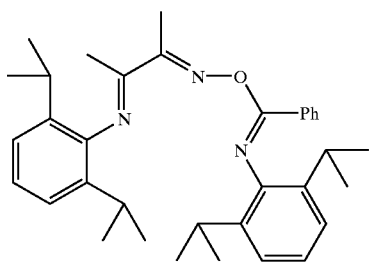

(Ib) 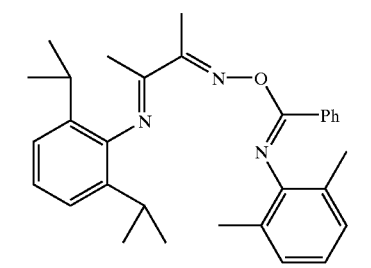

(Ic) 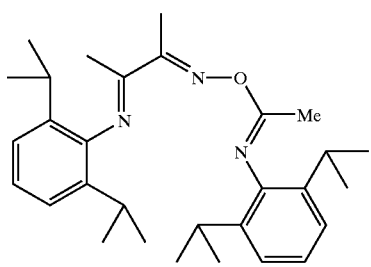

(Id) 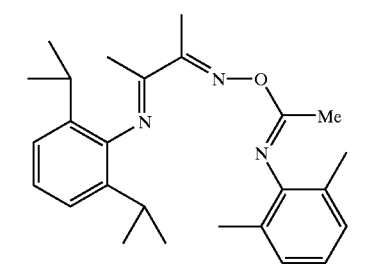

(Ie) 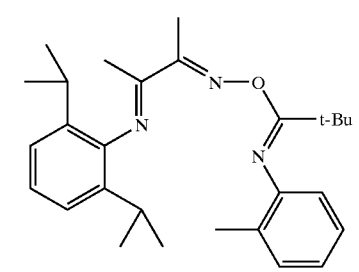

(IIIa) 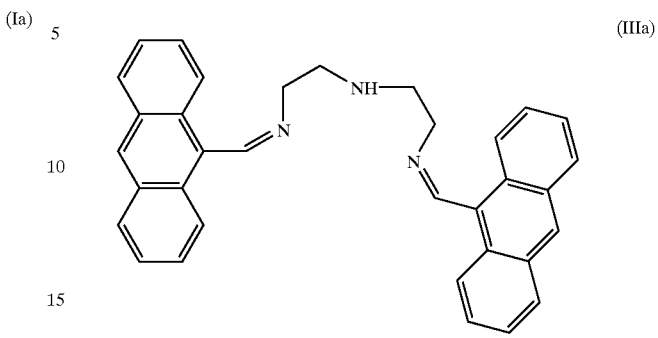

Included within the meaning of compounds (VII) and (X) are agostic structures in which the ethylene is replaced as a ligand by coordination to $-PZ^2$ to form an agostic "bidentate" ligand.

In the second polymerization process described herein an iron or cobalt complex (II) or (IV) is contacted with ethylene and a neutral Lewis acid W capable of abstracting X−, hydride or alkyl from (II) or (IV) to form a weakly coordinating anion, and must alkylate or be capable of adding a hydride ion to the metal atom, or an additional alkylating agent or an agent capable of adding a hydride anion to the metal atom must be present. The neutral Lewis acid is originally uncharged (i.e., not ionic). Suitable neutral Lewis acids include $SbF_5$, $Ar_3B$ (wherein Ar is aryl), and $BF_3$. In those instances in which (II) or (IV) (and similar catalysts which require the presence of a neutral Lewis acid), does not contain an alkyl or hydride group already bonded to the metal atom, the neutral Lewis acid or a cationic Lewis or Bronsted acid also alkylates or adds a hydride to the metal or a separate alkylating or hydriding agent is present, i.e., causes an alkyl group or hydride to become bonded to the metal atom.

It is preferred that $R^{20}$ contains 1 to 4 carbon atoms, and more preferred that $R^{20}$ is methyl or ethyl.

For instance, alkyl aluminum compounds (see next paragraph) may alkylate (II). However, not all alkyl aluminum compounds may be strong enough Lewis acids to abstract X− or an alkyl group from the metal atom. In that case a separate Lewis acid strong enough to do the abstraction must be present.

A preferred neutral Lewis acid, which can alkylate the metal, is a selected alkyl aluminum compound, such as $R^{19}_3Al$, $R^{19}AlCl_2$, $R^{19}_2AlCl$, and "$R^{19}AlO$" (alkylaluminoxanes), wherein $R^{19}$ is alkyl containing 1 to 25 carbon atoms, preferably 1 to 4 carbon atoms. Suitable alkyl aluminum compounds include methylaluminoxane (which is an oligomer with the general formula $[MeAlO]_n$), optionally modified with minor amounts of other alkyl groups, $(C_2H_5)_2AlCl$, $C_2H_5AlCl_2$, and $[(CH_3)_2CHCH_2]_3Al$.

Metal hydrides such as $NaBH_4$ may be used to bond hydride groups to the metal M.

The polymerization catalysts and catalyst systems described herein may produce polyethylene in a variety of molecular weights and molecular weight distributions. The molecular weights of these polymers may vary from compounds containing only a few ethylene molecules (e.g., oligomers) to polymers having molecular weights in the hundreds of thousands, and even higher. The molecular weight of the polymer produced in any particular polymerization process will depends on the process conditions used, and on the compound [such as (I) and (III)] which is used in the polymerization catalyst system. In one form of "chain transfer" in the polymerization process it is believed that an olefinic group is formed on the end of the polymer chain (see Examples 23–44, wherein Mn is measured by $^1$H NMR assuming all olefinic groups are end groups). If the olefinic group is on the end of a linear polymer chain that happens to be a relatively short polymer chain (say containing 4 to about 30 carbon atoms) the product is sometimes termed a linear α-olefin (LAO). LAOs are important items of commerce, useful as monomers and as chemical intermediates for items such as detergents and lubricating oils. For making LAOs it is preferred that in (I) and (III), and their Fe and Co complexes, that $Ar^1$ and $Ar^2$ are independently phenyl or 2-substituted phenyl, or $Ar^3$ and $Ar^4$ are independently phenyl or 2-substituted phenyl, for and $Ar^4$ are independently phenyl or 2-substituted phenyl, for example 2-methylphenyl or 2-i-propylphenyl.

Compounds such as (I) may b e mad e by reacting an appropriate dicarbonyl compound with one mole of hydroxylamine to form the monooxime. This oxime containing a second carbonyl group is then reacted with an arylamine to form the imine-oxime. The anion of the oxime is then formed by reaction with a strong base, such as an alkali metal hydride, followed by reaction with an appropriate chloroimine to form (I). The chloroimines are made by reaction of the appropriate amide with a chlorinating agent such as $PCl_5$. These various reactions are illustrated herein in Examples 1–9.

(III) may be made by the reaction of the appropriate diethylenetriamine (or appropriate analog) with a carbonyl substituted aryl compound.

Complexes of (I) or (III) with Fe or Co may be made by methods known in the art, see for instance previously incorporated U.S. Pat. No. 5,955,555, wherein the preparation of Fe and Co complexes of pyridinebisimines are described. Analogous methods may be used to make complexes of (I) and (III).

In all the polymerization processes herein, the temperature at which the polymerization is carried out is about −100° C. to about +200° C., preferably about 0° C. to about 150° C., more preferably about 25° C. to about 100° C. The ethylene concentration at which the polymerization is carried out is not critical, atmospheric pressure to about 275 MPa being a suitable range for ethylene.

The polymerization processes herein may be run in the presence of various liquids, particularly aprotic organic liquids. The catalyst system, ethylene, and polyethylene may be soluble or insoluble in these liquids, but obviously these liquids should not prevent the polymerization from occurring. Suitable liquids include alkanes, cycloalkanes, selected halogenated hydrocarbons, selected aromatic halogenated hydrocarbons, and aromatic hydrocarbons. Hydrocarbons are the preferred solvent. Specific useful solvents include hexane, heptane, toluene, benzene, chlorobenzene, methylene chloride, 1,2,4-trichlorobenzene, p-xylene, and cyclohexane.

The catalysts herein may be "heterogenized" by coating or otherwise attaching them to solid supports, such as silica or alumina. Where an active catalyst species is formed by reaction with a compound such as an alkylaluminum compound, a support on which the alkylaluminum compound is first coated or otherwise attached is contacted with the iron or cobalt compound precursor to form a catalyst system in which the active iron or cobalt catalyst is "attached" to the solid support. These supported catalysts may be used in polymerizations in organic liquids, as described in the immediately preceding paragraph. They may also be used in so-called gas phase polymerizations in which the ethylene being polymerized is added to the polymerization as a gas and no liquid supporting phase is present.

The polymerization processes described herein may be run in any manner common for coordination olefin polymerization processes, such as batch, semi-batch, and continuous. Processes applicable generally to Ziegler-Natta and metallocene-type polymerization catalysts may also be used in the present processes. The processes may be run in solution, slurry or gas phases.

It is believed that usually the homopolyethylene produced by the present polymerization processes are fairly linear polymers with little branching.

It is known that certain transition metal containing polymerization catalysts are especially useful in varying the branching in polyolefins made with them, see for instance U.S. Pat. No. 5,714,556, U.S. Pat. No. 5,880,241, WO98/30610 and WO98/30609 (all of which are incorporated by reference herein for all purposes). It is also known that blends of distinct polymers, that vary for instance in branching, molecular weight, and/or molecular weight distribution, may have advantageous properties compared to "single" polymers. For instance it is known that polymers with broad or bimodal molecular weight distributions may be melt processed (be shaped) more easily than narrower molecular weight distribution polymers. Similarly, thermoplastics such as crystalline polymers may often be toughened by blending with elastomeric polymers.

Therefore, methods of producing polymers which inherently produce polymer blends are useful especially if a later separate (and expensive) polymer mixing step can be avoided. However in such polymerizations one should be aware that two different catalysts may interfere with one another, or interact in such a way as to give a single polymer.

In such a process the catalysts disclosed herein can be termed the first active polymerization catalyst. Monomers useful with these catalysts are those described (and also preferred) above.

A second active polymerization catalyst (and optionally one or more others) is used in conjunction with the first active polymerization catalyst. The second active polymerization catalyst may be another late transition metal catalyst, for example as described in previously incorporated WO98/30610, WO98/30609, U.S. Pat. No. 5,714,556, U.S. Pat. No. 5,880,241 and U.S. Pat. No. 5,955,555.

Other useful types of catalysts may also be used for the second active polymerization catalyst. For instance so-called Ziegler-Natta and/or metallocene-type catalysts may also be used. These types of catalysts are well known in the polyolefin field, see for instance *Angew. Chem., Int. Ed. Engl.*, vol. 34, p. 1143–1170 (1995), EP-A-0416815 and U.S. Pat. No. 5,198,401 for information about metallocene-type catalysts, and J. Boor Jr., *Ziegler-Natta Catalysts and Polymerizations*, Academic Press, New York, 1979 for information about Ziegler-Natta-type catalysts, all of which are hereby included by reference. Many of the useful polymerization conditions for all of these types of catalysts and the first active polymerization catalysts coincide, so conditions for the polymerizations with first and second active polymerization catalysts are easily accessible. Oftentimes the "co-catalyst" or "activator" is needed for metallocene or Ziegler-Natta-type polymerizations. In many instances the same compound, such as an alkylaluminum compound, may be used as an "activator" for some or all of these various polymerization catalysts.

Suitable catalysts for the second polymerization catalyst also include metallocene-type catalysts, as described in U.S. Pat. No. 5,324,800 and EP-0129368; particularly advantageous are bridged bis-indenyl metallocenes, for instance as described in U.S. Pat. No. 5,145,819 and EP-A-0485823. Another class of suitable catalysts comprises the well-known constrained geometry catalysts, as described in EP-A-0416815, EP-A-0420436, EP-A-0671404, EP-A-0643066 and WO91/04257. Finally, the class of transition metal complexes described in WO96/13529 can be used. All of the above-mentioned publications are hereby included by reference herein.

In one preferred process described herein the first olefin(s) [the monomer(s), usually ethylene, polymerized by the first active polymerization catalyst] and second olefin(s) [the monomer(s) polymerized by the second active polymerization catalyst] are identical, and preferred olefins in such a process are the same as described immediately above. The first and/or second olefins may also be a single olefin or a mixture of olefins to make a copolymer. Again it is preferred that they be identical particularly in a process in which polymerization by the first and second active polymerization catalysts make polymer simultaneously.

In some processes herein the first active polymerization catalyst may polymerize a monomer that may not be polymerized by said second active polymerization catalyst, and/or vice versa. In that instance two chemically distinct polymers may be produced. In another scenario two monomers would be present, with one polymerization catalyst producing a copolymer, and the other polymerization catalyst producing a homopolymer, or two copolymers may be produced which vary in the molar proportion or repeat units from the various monomers. Other analogous combinations will be evident to the artisan.

In another variation of this process one of the polymerization catalysts makes an oligomer of an olefin, preferably ethylene, which oligomer has the formula $R^{70}CH=CH_2$, wherein $R^{70}$ is n-alkyl, preferably with an even number of carbon atoms. The other polymerization catalyst in the process then (co)polymerizes this olefin, either by itself or preferably with at least one other olefin, preferably ethylene, to form a branched polyolefin. Preparation of the oligomer (which is sometimes called an α-olefin) by a second active polymerization-type of catalyst can be found in previously incorporated U.S. Pat. No. 5,880,241, and WO99/02472 (also incorporated by reference herein for all purposes).

Likewise, conditions for such polymerizations, using catalysts of the second active polymerization type, will also be found in the appropriate above mentioned references.

Two chemically different active polymerization catalysts are used in this polymerization process. The first active polymerization catalyst is described in detail above. The second active polymerization catalyst may also meet the limitations of the first active polymerization catalyst, but must be chemically distinct. For instance, it may have a different transition metal present, and/or utilize a different type of ligand and/or the same type of ligand which differs in structure between the first and second active polymerization catalysts. In one preferred process, the ligand type and the metal are the same, but the ligands differ in their substituents.

Included within the definition of two active polymerization catalysts are systems in which a single polymerization catalyst is added together with another ligand, preferably the same type of ligand, which can displace the original ligand coordinated to the metal of the original active polymerization catalyst, to produce in situ two different polymerization catalysts.

The molar ratio of the first active polymerization catalyst to the second active polymerization catalyst used will depend on the ratio of polymer from each catalyst desired, and the relative rate of polymerization of each catalyst under the process conditions. For instance, if one wanted to prepare a "toughened" thermoplastic polyethylene that contained 80% crystalline polyethylene and 20% rubbery polyethylene, and the rates of polymerization of the two catalysts were equal, then one would use a 4:1 molar ratio of the catalyst that gave crystalline polyethylene to the catalyst that gave rubbery polyethylene. More than two active polymerization catalysts may also be used if the desired product is to contain more than two different types of polymer.

The polymers made by the first active polymerization catalyst and the second active polymerization catalyst may be made in sequence, i.e., a polymerization with one (either first or second) of the catalysts followed by a polymerization with the other catalyst, as by using two polymerization vessels in series. However it is preferred to carry out the polymerization using the first and second active polymerization catalysts in the same vessel(s), i.e., simultaneously. This is possible because in most instances the first and second active polymerization catalysts are compatible with each other, and they produce their distinctive polymers in the other catalyst's presence. Any of the processes applicable to the individual catalysts may be used in this polymerization process with 2 or more catalysts, i.e., gas phase, liquid phase, continuous, batch etc.

The polymers produced by this "mixed catalyst" process may vary in molecular weight and/or molecular weight distribution and/or melting point and/or level of crystallinity, and/or glass transition temperature and/or other factors. For copolymers the polymers may differ in ratios of comonomers if the different polymerization catalysts polymerize the monomers present at different relative rates. The polymers produced are useful as molding and extrusion resins and in films as for packaging. They may have advantages such as improved melt processing, toughness and improved low temperature properties.

Hydrogen may be used to lower the molecular weight of polyethylene produced in the first, second or third processes, or any other processes mentioned above in which the present transition metal complexes are used. It is preferred that the amount of hydrogen present be about 0.01 to about 50 mole percent of the ethylene present, preferably about 1 to about 20 mole percent. The relative concentrations of ethylene and hydrogen may be regulated by their partial pressures.

Included herein within the definitions of all the polymerization processes are mixtures of starting materials that lead to the formation in situ of the transition metal compounds specified in all of the polymerization processes.

In the first, second and third polymerization process, and other polymerization processes herein one or more olefins of the formula $R^{15}CH=CH_2$ may be homopolymerized or copolymerized with each and/or with ethylene using the iron and cobalt complex of (I) and (III), as described herein. Similar (to ethylene polymerization) process conditions may be used to carry out these polymerizations.

The polymers produced by the present processes are useful as molding resins, for films and other uses. End use areas include industrial and consumer parts and packaging.

In the Examples, the following abbreviations are used:

Ar—aryl
Et—ethyl
GPC—gel permeation chromatography
Me—methyl
MI—melt index
PE—polyethylene
Ph—phenyl
RT—room temperature
TCB—1,2,4-trichlorobenzene
THF—tetrahydrofuran
TO—turnovers

EXAMPLE 1

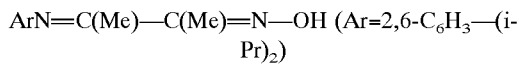

2,3-Butanedione monooxime (20.753 g, 0.205 mmol) and 2,6-diisopropylaniline (47.31 g, 0.267 mol, 1.30 equiv.) were dissolved in ~100 mL of methanol along with 10 drops of formic acid. The reaction mixture was stirred several days. A white precipitate formed, which was collected on a frit and then dissolved in methylene chloride; the resulting solution was stirred overnight over sodium sulfate. The mixture was then filtered through a frit with Celite®, the solvent was removed and the product was dried in vacuo to yield 30.71 g of a white powder. An additional 11.57 g of product was obtained by concentrating the remaining methanol solution (79.1% total yield): $^1$H NMR (CDCl$_3$, 500 MHz) δ 8.32 (s, 1, OH), 7.07 (d, 2, H$_{aryl}$), 7.00 (t, 1, H$_{aryl}$), 2.54 (septet, 2, CHMe$_2$), 2.20 and 1.81 (s, 3 each, N=C(Me)—C'(Me)=N), 1.06 and 1.08 (d, 6 each, CHMeMe'); $^{13}$C NMR (CDCl$_3$, 125 MHz) δ 163.9 and 158.6 (N=C—C'=N), 145.7 (Ar:C$_{ipso}$) 135.3, 123.6 and 122.9 (Ar:$_{Co,m,p}$), 28.2 (CHMe$_2$), 23.0 and 22.7 (CHMeMe'), 16.3 and 9.3 (N=C(Me)—C'(Me)=N). The structure of this compound was confirmed by X-ray crystal structure analysis.

EXAMPLE 2

ArN=C(Me)—C(Me)=N—ONa (Ar=2,6-C$_6$H$_3$—(i-Pr)$_2$)

In a nitrogen-filled drybox, ArN=C(Me)—C(Me)=N—OH (Ar=2,6-C$_6$H$_3$—(i-Pr)$_2$ (3.652 g, 14.03 mmol) was dissolved in ~100 mL of THF. Sodium hydride (0.660 g, 27.5 mmol, 1.96 equiv) was slowly added to the flask and the reaction mixture was stirred for four days. The reaction mixture was then filtered through a frit with Celite® and the THF was removed in vacuo to yield 3.43 g of yellow powder (87% yield): $^1$H NMR (THF-d$_8$, 300 MHz) δ 7.03 (d, 2, H$_{aryl}$), 6.89 (t, 1, H$_{aryl}$) 2.73 (septet, 2, CHMe$_2$), 2.17 and 1.91 (s, 3, each, N=C(Me)-C'(Me)=N), 1.12 and 1.08 (d, 6 each, CHMeMe'). (Note: Reaction times for this deprotonation are variable. Prior to work-up, the $^1$H NMR spectrum of a small sample of the reaction mixture was typically checked for the —OH resonance to determine if the reaction was complete.)

EXAMPLE 3

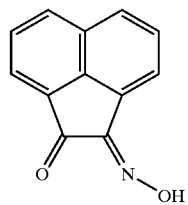

Acenaphthenequinone (10.00 g, 54.89 mmol) and hydroxylamine hydrochloride (3.814 g, 54.89 mmol) were dissolved in a mixture of 50 mL of ethanol, 50 mL of dichloromethane, and 50 mL of pyridine. The reaction mixture was stirred for several days before adding water and extracting the product with dichloromethane. The dichloromethane solution was stirred overnight over sodium sulfate and then the mixture was filtered through a frit with Celite®. The solvent was removed and the resulting pale orange powder (9.871 g, 91.2%) was dried in vacuo: $^1$H NMR (N,N-dimethylformamide-d$_7$, 500 MHz) δ 11.85 (br s, 1, N—OH), 8.72 (d, 1, H$_{aryl}$), 8.69 (d, 1, H$_{aryl}$), 8.55 (d, 1, H$_{aryl}$), 8.40 (d, 1, H$_{aryl}$), 8.24 (t, 1, H$_{aryl}$), 8.18 (t, 1, H$_{aryl}$).

EXAMPLE 4

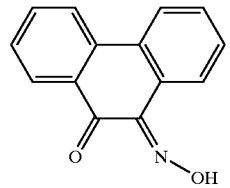

Phenanthrenequinone (2.00 g, 9.61 mmol) and hydroxylamine hydrochloride (0.6675 g, 9.61 mmol) were dissolved in a mixture of 10 mL of ethanol, 10 mL of dichloromethane, and 10 mL of pyridine. The reaction mixture was stirred for several days before adding water and extracting the product with dichloromethane. The dichloromethane solution was stirred overnight over sodium sulfate and then filtered through a frit with Celite®. The solvent was removed and the resulting orange powder (1.83 g, 85.3%) was dried in vacuo: $^1$H NMR (CDCl$_3$, 500 MHz) δ 8.34 (d, 1, H$_{aryl}$), 8.28 (d, 1, H$_{aryl}$), 8.10 (d, 1, H$_{aryl}$), 8.03 (d, 1, H$_{aryl}$), 7.72 (t, 1, H$_{aryl}$), 7.47 (t, 1, H$_{aryl}$), 7.46 (t, 1, H$_{aryl}$), 7.40 (t, 1, H$_{aryl}$); $^{13}$C NMR (CDCl$_3$, 125 MHz) δ 182.1 (C=O), 143.9 (C=N), 137.4–123.1 (C$_{aryl}$).

EXAMPLES 5–9

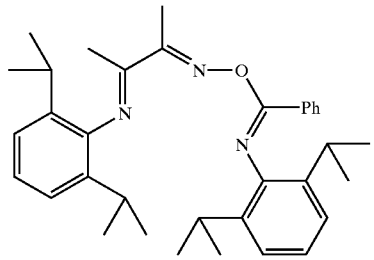

(Ia)

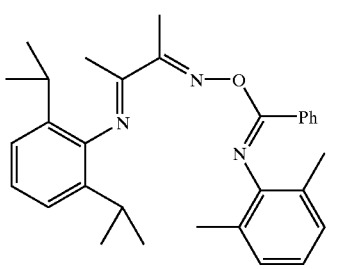

(Ib)

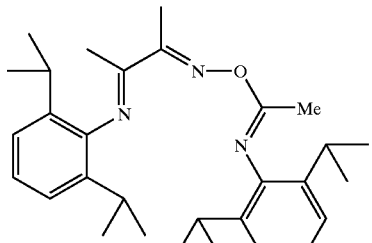

(Ic)

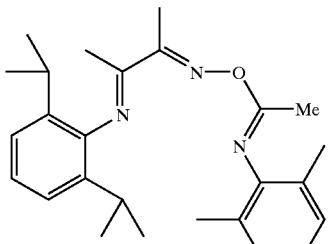

(Id)

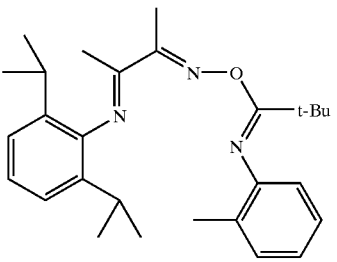

(Ie)

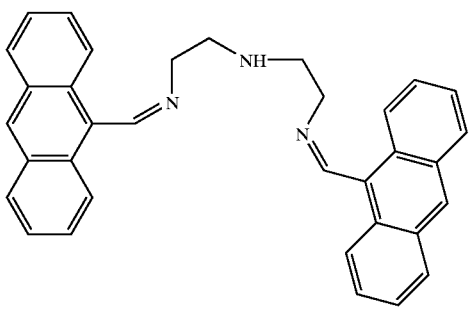

(IIIa)

The procedures for the syntheses of ligands (Ia–e) and (IIa) are given in the examples below.

Synthesis of Amides. The amide precursors to the chloroimines were either obtained from commercial sources [e.g., MeC(O)NHAr (Ar=2,6-C$_6$H$_3$-Me$_2$) and t-BuC(O)NHAr (Ar=2-C$_6$H$_4$-Me)] or synthesized according to the following general procedure [e.g., PhC(O)NHAr (Ar=2,6-C$_6$H$_3$—(i-Pr)$_2$, PhC(O)NHAr (Ar=2,6-C$_6$H$_3$-Me$_2$), MeC(O)NHAr (Ar=2,6-C$_6$H$_3$—(i-Pr)$_2$]: A dry Schlenk flask was attached to a Schlenk line, evacuated, and back-filled with argon. Dry solvent (~300 mL of either hexanes or toluene), the aniline (~113 mmol), and 1.3 equiv of triethylamine were placed in the Schlenk flask. A dry addition funnel was attached to the Schlenk flask and a solution of the acid halide (1.1 equiv) in the dry solvent (~50 mL of either hexanes or toluene) was placed in the addition funnel. The flask was cooled to 0° C. and the acid halide solution was slowly added to the flask. After the addition was complete, the reaction mixture was allowed to warm to room temperature and then stirred overnight. A precipitate formed and, if necessary, additional solvent was added to enable stirring. Next, water was added to the flask and the resulting mixture was stirred well. The remaining precipitate was collected on a frit and washed with water and then petroleum ether. The solid was dissolved in THF and the resulting solution was stirred overnight over sodium sulfate. The mixture was filtered through a frit with Celite®, the solvent was evaporated, and the white powder was dried in vacuo. $^1$H NMR spectra of the resulting amides are reported below.

PhC(O)NHAr (Ar=2,6-C$_6$H$_3$—(i-Pr)$_2$. Synthesized from PhC(O)Cl and ArNH$_2$: $^1$H NMR (THF-d$_8$, 500 MHz) δ 9.02 (br s, 1, NH), 7.97 (d, 2, C$_{ph}$), 7.50 (t, 1, C$_{ph}$), 7.41 (t, 2, C$_{ph}$), 7.30 (t, 1, C$_{aryl}$), 7.20 (d, 2, C$_{aryl}$), 3.22 (septet, 2, ChMe$_2$), 1.21 (d, 12, CHMe$_2$).

PhC(O)NHAr (Ar=2,6-C$_6$H$_3$-Me$_2$). Synthesized from PhC(O)Cl and ArNH$_2$: $^1$H NMR (CDCl$_3$, 500 MHz) δ 7.93 (d, 2, C$_{ph}$), 7.61 (br s, 1, NH), 7.58 (t, 1, C$_{ph}$), 7.51 (t, 2, C$_{ph}$), 7.15 (m, 3, H$_{aryl}$), 2.29 (s, 6, Me).

MeC(O)NHAr (Ar=2,6-C$_6$H$_3$—(i-Pr)$_2$. Synthesized from MeC(O)Cl and ArNH$_2$: $^1$H NMR (CDCl$_3$, 500 MHz) Two isomers are present. Major isomer: δ 7.17 (t, 1, C$_{aryl}$), 7.15 (br s, 1, NH), 7.03 (d, 2, H$_{aryl}$), 2.92 (septet, 2, CHMe$_2$), 2.12 (s, 3, Me), 1.16 (d, 12, CHMe$_2$); Minor isomer: δ 7.48 (s, 1, NH), 7.22 (t, 1, H$_{aryl}$), 7.09 (d, 2, H$_{aryl}$), 3.01 (septet, 2, CHMe$_2$), 1.68 (s, 3, Me), 1.22 and 1.14 (d, 6 each, CHMeMe').

Synthesis of Chloroimines. The chloroimines [ArN=C(Cl)(Ph) (Ar=2,6-C$_6$H$_3$—(i-Pr)$_2$), ArN=C(Cl)(Ph) (Ar=2,6-C$_6$H$_3$-Me$_2$), ArN=C(Cl)(Me) (Ar=2,6-C$_6$H$_3$—(i-Pr)$_2$), ArN=C(Cl)(Me) (Ar=2,6-C$_6$H$_3$-Me$_2$), and ArN=C(Cl)(t-Bu) (Ar=2-C$_6$H$_4$-Me) were synthesized according to the following general procedure: In a nitrogen-filled drybox, the amide (~90 mmol) was placed in a Schlenk flask and suspended in ~100 mL of dry toluene. PCl$_5$ (1.1 equiv) was added to the toluene suspension, and then the Schlenk flask was capped with a septum and removed from the drybox. In a fume hood, the septum was removed from the flask and the flask was quickly connected to a reflux condenser attached to a nitrogen source and a NaOH(aq) trap. The reaction mixture was refluxed until HCl evolution had ceased (typically ~1 day). The reaction mixture was allowed to cool to RT. The reflux condenser was removed and the flask was quickly capped with a septum and attached to a Schlenk line. A cannula-filter was used to filter the solution and transfer it into another Schlenk flask. The solvent was evaporated to yield the chloroimine as either a powder or an oil, and the evacuated flask was then brought back into the drybox. In the drybox, further purification of the product was sometimes carried out by dissolving the chloroimine in pentane and filtering the solution through a frit with Celite® and removing the solvent in vacuo. $^1$H NMR spectra of the chloroimines were obtained and are reported below. Absence of phosphorus-containing by-products was confirmed by $^{31}$P NMR spectroscopy.

ArN=C(Cl)(Ph) (Ar=2,6-C$_6$H$_3$—(i-Pr)$_2$). Synthesized from PhC(O)NHAr: $^1$H NMR (CDCl$_3$, 500 MHz) δ 8.28 (d, 2, $C_{ph}$), 7.62 (t, 1, $C_{ph}$), 7.56 (t, 2, $C_{ph}$), 7.25 (m, 3, $C_{aryl}$), 2.90 (septet, 2, CHMe$_2$), 1.30 and 1.23 (CHMeMe').

ArN=C(Cl)(Ph) (Ar=2,6-C$_6$H$_3$-Me$_2$). Synthesized from PhC(O)NHAr: $^1$H NMR (CDCl$_3$, 500 MHz) δ 8.27 (d, 2, $C_{ph}$), 7.62 (t, 1, $C_{ph}$), 7.55 (t, 2, $C_{ph}$), 7.15 (d, 2, $C_{aryl}$), 7.09 (t, 1, $C_{aryl}$), 2.18 (s, 6, Me).

ArN=C(Cl)(Me) (Ar=2,6-C$_6$H$_3$—(i-Pr)$_2$). Synthesized from MeC(O)NHAr: $^1$H NMR (C$_6$D$_6$, 500 MHz) δ 7.23 (m, 3, H$_{aryl}$), 3.05 (septet, 2, CHMe$_2$), 2.28 (s, 3, Me), 1.5–1.2 (br m, 12, CHMeMe').

ArN=C(Cl)(Me) (Ar=2,6-C$_6$H$_3$-Me$_2$). Synthesized from MeC(O)NHAr: $^1$H NMR (CDCl$_3$, 500 MHz) δ 7.13 (d, 2, H$_{aryl}$), 7.07 (t, 1, H$_{aryl}$), 2.70 (s, 3, Me), 2.19 (s, 6, Ar:Me).

ArN=C(Cl)(t-Bu) (Ar=2-C$_6$H$_4$-Me). Synthesized from t-BuC(O)NHAr: $^1$H NMR (C$_6$D$_6$, 500 MHz) δ 7.17 (t, 1, H$_{aryl}$), 7.16 (d, 1, H$_{aryl}$), 7.05 (t, 1, H$_{aryl}$), 6.87 (d, 1, H$_{aryl}$), 2.17 (s, 3, Me), 1.37 (s, 9, CMe$_3$).

EXAMPLE 5

Ligand (Ia)

In a nitrogen-filled drybox, ArN=C(Me)—C(Me)=N—ONa (Ar=2,6-C$_6$H$_3$—(i-Pr)$_2$) (0.891 g, 3.16 mmol) and ArN=C(Cl)(Ph) (Ar=2,6-C$_6$H$_3$—(i-Pr)$_2$) (1.04 g, 3.47 mmol, 1.10 equiv) were dissolved together in ~40 mL of Et$_2$O. The reaction mixture was stirred overnight and then filtered through a frit with Celite®. The Et$_2$O was removed in vacuo, and the product mixture was dissolved in pentane. The pentane solution was filtered and then the solvent was removed in vacuo to obtain 1.4 g (85%) of (Ia) as a yellow powder: $^1$H NMR (THF-d$_8$, 500 MHz, 25° C.) δ 8.15 (d, 2, H$_{ph}$), 7.56–7.44 (m, 3, H$_{ph}$), 7.07 (d, 2, H$_{aryl}$), 6.99 (d, 2, H$_{aryl}$), 6.97 (t, 1, H$_{aryl}$), 6.84 (t, 1, H$_{aryl}$), 2.98 and 2.46 (septet, 2 each, CHMe$_2$ and C'HMe$_2$), 2.30 and 1.11 (s, 3 each, N=C(Me)—C'(Me)=N), 1.16, 1.14, 1.08 and 1.05 (d, 6 each, CHMeMe' and C'HMeMe'). The structure of this compound was confirmed by X-ray crystal structure analysis.

EXAMPLE 6

Ligand (Ib)

In a nitrogen-filled drybox, ArN=C(Me)—C(Me)=N—ONa (Ar=2,6-C$_6$H$_3$—(i-Pr)$_2$) (0.833 g, 2.95 mmol) and ArN=C(Cl)(Ph) (Ar=2,6-C$_6$H$_3$-Me$_2$) (0.724 g, 2.97 mmol, 1.01 equiv) were dissolved together in ~40 mL of Et$_2$O. The reaction mixture was stirred overnight and then filtered through a frit with Celite®. The Et$_2$O was removed in vacuo, and the product mixture was dissolved in pentane. The pentane solution was filtered and then the solvent was removed in vacuo. Next the product was dissolved in benzene and filtered through basic alumina. The benzene was removed in vacuo to yield 0.841 g (61%) of (Ib): $^1$H NMR (C$_6$D$_6$, 500 MHz, 25° C.) δ 8.37 (br m, 2, H$_{aryl}$), 7.35–7.16 (m, 3, H$_{aryl}$), 7.05 (d, 2, H$_{ph}$), 6.93 (t, 1, H$_{ph}$), 2.68 (septet, 2, CHMe$_2$), 2.33 (s, 3, N=C(Me)—C'(Me)=N), 2.31 (s, 6, Ar:Me), 1.42 (br s, 3, N=C(Me)—C'(Me)=N), 1.23 and 1.21 (d, 6 each, CHMeMe').

EXAMPLE 7

Ligand (Ic)

In a nitrogen-filled drybox, ArN=C(Me)—C(Me)=N—ONa (Ar=2,6-C$_6$H$_3$—(i-Pr)$_2$) (0.218 g, 0.772 mmol) and ArN=C(Cl)(Me) (Ar=2,6-C$_6$H$_3$—(i-Pr)$_2$) (0.186 g, 0.782 mmol, 1.01 equiv) were dissolved together in ~40 mL of a 1:3 mixture of THF and pentane. The reaction mixture was stirred overnight and then the solvent was removed in vacuo. The product mixture was dissolved in pentane and the resulting solution was filtered through a frit with Celite®. The pentane was removed in vacuo to yield (Ic): $^1$H NMR (C$_6$D$_6$, 400 MHz, 75° C.) δ 7.13–7.01 (m, 6, H$_{aryl}$), 3.14 (septet, 2, CPMe$_2$), 2.59 (septet, 2, C'HMe$_2$), 2.13 and 1.80 (br s, 6 and 3 each, N=C(Me)—C'(Me)=N and OC(Me)=N), 1.21, 1.07 and 1.06 (d; 12, 6 and 6 each; CHMeMe' and C'HMeMe').

EXAMPLE 8

Ligand (Id)

In a nitrogen-filled drybox, a solution of ArN=C(Cl)(Me) (Ar=2,6-C$_6$H$_3$-Me$_2$) (0.459 g, 2.53 mmol, 1.02 equiv) in 25 mL of Et$_2$O was slowly added over a 30 min. period to a 25 mL Et$_2$O solution of ArN=C(Me)—C(Me)=N—ONa (Ar=2,6-C$_6$H$_3$—(i-Pr)$_2$) (0.699 g, 2.47 mmol). The reaction mixture was stirred overnight, 150 mL of pentane was added, and the resulting solution was filtered through a frit with Celite®. The solvent was removed in vacuo, and the product mixture was dissolved in benzene. The benzene solution was filtered through basic alumina and then the solvent was removed in vacuo to yield (Id): $^1$H NMR (C$_6$D$_6$, 500 MHz, 25° C.) δ 7.27–6.73 (m, 6, H$_{aryl}$), 2.75–2.48 (br septets, 2, CHMe$_2$), 2.42–2.02, 1.95 and 1.71 (br singlets; 9, 3 and 3 each; N=C(Me)—C'(Me)=N, Ar:Me$_2$, and OC(Me)=N), 1.08 (br resonance with a sharp doublet superimposed, 12, CHMeMe').

EXAMPLE 9

Ligand (Ie)

In a nitrogen-filled drybox, ArN=C(Me)—C(Me)=N—ONa (Ar=2,6-C$_6$H$_3$—(i-Pr)$_2$) (0.827 g, 2.93 mmol) and ArN=C(Cl)(t-Bu) (Ar=2-C$_6$H$_4$-Me) (0.612 g, 2.92 mmol, 1.00 equiv) were dissolved together in ~40 mL of Et$_2$O. The reaction mixture was stirred overnight and then filtered through a frit with Celite® to yield 0.917 g of (Ie) as a pale orange oil: $^1$H NMR (THF-d$_8$, 500 MHz, 25° C.) δ 7.07–7.02 (m, 2, H$_{aryl}$), 6.98–6.87 (m, 3, H$_{aryl}$), 6.69 (t, 1, H$_{aryl}$), 6.55 (d, 1, H$_{aryl}$), 2.42 (septet, 2, CHMe$_2$), 2.17 and 2.08 (s, 3 each, N=C(Me)C'(Me)=N and Ar:Me), 1.40 (s, 9, CMe$_3$), 1.12 (s, 3, N=C(Me)—C'(Me)=N), 1.06 and 1.03 (d, 6 each, CHMeMe').

EXAMPLE 10

Ligand (IIa)

Diethylenetriamine (2.272 g, 22.02 mmol) and 9-anthraldehyde (9.538 g, 46.25 mmol, 2.10 equiv) were dissolved in methanol along with 10 drops of formic acid. Within 15 minutes of mixing, a precipitate formed. The reaction mixture was stirred overnight, and then the precipitate was collected on a frit, washed with methanol and dissolved in CH$_2$Cl$_2$. The CH$_2$Cl$_2$ solution was stirred overnight over sodium sulfate and then filtered through a frit with Celite®. The solvent was removed and the resulting orange powder (9.248 g, 87.56%) was dried in vacuo. The $^1$H NMR spectrum is consistent with the isolation of (IIa) (~90%) along with small amounts of by-products including 9-anthraldehyde and the mono-imine intermediate: $^1$H NMR (CDCl$_3$, 500 MHz) δ 9.46 (s, 2, N=CH or H$_{aryl}$), 8.47 (m, 4, H$_{aryl}$), 8.39 (s, 2, N=CH or H$_{aryl}$) 7.92 (m, 4, H$_{aryl}$), 7.38

(m, 8, $H_{aryl}$), 4.11 (t, 4, $NCH_2CH_2N'$), 3.30 (t, 4, $NCH_2CH_2N'$), 2.07 (br s, 1, NH).

EXAMPLES 11–20

General Procedure for the Synthesis of $CoCl_2$ and $FeCl_2$ Complexes

In a nitrogen-filled drybox, a mixture of the ligand and $MCl_2$ (M=Co or Fe) in ~5 mL of THF was stirred for one to several days. The THF solution was then filtered through a frit with Celite® and the solvent was removed in vacuo. Next, the solid was dissolved in toluene and the resulting solution was filtered through a frit with Celite®. The toluene was evaporated and the resulting powder was washed with pentane and dried in vacuo.

EXAMPLE 11

(Ia)$COCl_2$

The above general procedure was followed using 630 mg (1.20 mmol) of (Ia) and 183 mg (1.41 mmol, 1.2 equiv) of $CoCl_2$ with the modification that following the evaporation of the THF, the product was dissolved in a 1:4 mixture of $Et_2O$/pentane and recrystallized to give 180 mg of a turquoise solid. The $Et_2O$/pentane was evaporated and the resulting solid was dissolved in toluene. The resulting solution was filtered and the solvent was removed to yield 97 mg of a light green solid (total yield: 35.7%).

EXAMPLE 12

(Ia)$FeCl_2$

The above general procedure was followed using 650 mg (1.24 mmol) of (Ia) and 164 mg (1.29 mmol, 1.04 equiv) of $FeCl_2$. A brown powder was isolated (582 mg, 72.1%).

EXAMPLE 13

(Ib)$CoCl_2$

The above general procedure was followed using 231 mg (0.494 mmol) of (Ib) and 62 mg (0.478 mmol, 0.968 equiv) of $CoCl_2$. A toluene-insoluble fraction (bright green powder, 125 mg, 43.8%) and toluene-soluble fraction (pale green powder, 10 mg, 3.50%) were isolated.

EXAMPLE 14

(Ib)$FeCl_2$

The above general procedure was followed using 278 mg (0.594 mmol) of (Ib) and 76 mg (0.60 mmol, 1.0 equiv) of $FeCl_2$. A toluene-soluble (brown powder, 170 mg, 48.1%) and toluene-insoluble (brown powder, 28 mg, 7.93%) fraction were isolated.

EXAMPLE 15

(Id)$CoCl_2$

The above general procedure was followed using 206 mg (0.508 mmol) of (Id) and 67 mg (0.52 mmol, 1.0 equiv) of $CoCl_2$. A moss green powder was isolated (105 mg, 38.6%).

EXAMPLE 16

(Id)$FeCl_2$

The above general procedure was followed using 244 mg (0.602 mmol) of (Id) and 82 mg (0.65 mmol, 1.1 equiv) of $FeCl_2$. A light red-tan powder was isolated (88 mg, 27.5%).

EXAMPLE 17

(Ie)$COCl_2$

The above general procedure was followed using 138 mg (0.318 mmol) of (Id) and 47.1 mg (0.363 mmol, 1.10 equiv) of $CoCl_2$ with the exception that following the evaporation of THF, the solid was not dissolved in toluene. Instead it was washed with pentane to give a green solid.

EXAMPLE 18

(Ie)$FeCl_2$

The above general procedure was followed using 95.5 mg (0.220 mmol) of (Ie) and 27.7 mg (0.219 mmol, 0.995 equiv) of $FeCl_2$ with the exception that following the evaporation of THF, the solid was not dissolved in toluene. Instead it was washed with pentane to give a brown solid.

EXAMPLE 19

(IIIa)$CoCl_2$

The above general procedure was followed using 1.0095 g (2.105 mmol) of (IIIa) and 0.2576 g (1.984 mmol, 0.94 equiv) of $CoCl_2$, and 20 mL of THF with the exception that the product was not soluble in THF. The tan precipitate was washed with THF, toluene and pentane and then dried in vacuo to yield 1.155 g (95.56%) of product.

EXAMPLE 20

(IIIa)$FeCl_2$

The above general procedure was followed using 1.0491 g (2.187 mmol) of (IIIa) and 0.2634 g (2.078 mmol, 0.95 equiv) of $FeCl_2$, and 20 mL of THF with the exception that the product was not soluble in THF. The red-orange precipitate was washed with THF, toluene and pentane and then dried in vacuo to yield 1.1583 g (91.92%) of product.

General Procedure for Ethylene Polymerizations and Copolymerizations for Tables 1–4

Procedure. A 30 mL glass vial equipped with a gas inlet and fitted glass cap was dried in the oven. Upon removal from the oven, the gas inlet of the vial was sealed with electrical tape and the vial was immediately pumped into a nitrogen-filled drybox. In the drybox, the glass vial was loaded with a cobalt or iron compound. Next, solvent was added to the glass vial and the vial was cooled in the drybox freezer to −30° C. The vial was briefly removed from the freezer while MMAO cocatalyst (1.7 molar in Al, heptane solution) and optionally comonomer was added and then placed back in the freezer to cool again. The cold vial was removed from the freezer, the top ground glass opening of the vial was greased and capped, and the vial was removed from the drybox. The vial was placed in a plastic bag and the bag was cooled in dry ice until the vial was loaded into a pressure tube and placed under ethylene; the electrical tape covering the gas inlet was removed immediately prior to this step. After the pressure tube was shaken mechanically for the stated reaction time, the ethylene pressure was released and the glass vial was removed from the pressure tube. The polymer was precipitated by the addition of MeOH (~20 mL) and concentrated HCl (~1–3 mL). The polymer was then collected on a frit and rinsed with MeOH. The polymer was transferred to a pre-weighed vial and dried under vacuum overnight. The polymer yield and characterization were then obtained. The following abbreviations are used in the Tables: TO: number of turnovers per metal center=(moles ethylene consumed, as determined by the weight of the isolated polymer or oligomers) divided by (moles catalyst); M.W.: Molecular weight of the polymer or oligomers as determined by melt index (MI: g/10 min at 190° C., 2160 g weight), GPC (molecular weights are reported versus polystyrene standards; conditions: Waters 150° C., trichlorobenzene at 150° C., Shodex® columns at −806MS 4G 734/602005, RI detector), and/or $^1$H NMR (olefin end group analysis); Total Me: Total number of methyl groups per 1000 methylene groups as determined by $^1$H NMR analysis.

In all of the Tables that follow "toluene-soluble" means that part of the transition metal compound that was soluble in toluene, while toluene-insoluble means that part of the transition metal compound which was insoluble in toluene. It is likely these fractions are the same compound, with the solubility of the compound in toluene not being high enough to dissolve all the transition metal compound present.

TABLE 1

Ethylene Polymerization
(5.9 MPa, p-Xylene (6 mL), 0.02 mmol cmpd, 18 h, 1 mL MMAO)

| Ex. | Cmpd | Temp (° C.) | PE(g) | PE(TO) |
|---|---|---|---|---|
| 21 | (Ie)FeCl$_2$ | 25 | 0.316 | 458 |
| 22 | (Ie)CoCl$_2$ | 25 | 0.309 | 549 |

TABLE 2

Ethylene Polymerization
(6.9 MPa, 1,2,4-Trichlorobenzene (8 mL), 0.02 mmol Cmpd, 18 h, 2 mL MMAO)

| Ex. | Cmpd | Temp (° C.) | PE(g) | PE(TO) | M.W. (MI, GPC, and/or $^1$H NMR) | Total Me |
|---|---|---|---|---|---|---|
| 23 | (Ia)FeCl$_2$ | 25 | 5.493 | 9,580 | MI < 0.01; M$_n$($^1$H):no olefins | 0.7 |
| 24 | (Ia)CoCl$_2$ | 25 | 0.11 | 188 | | |
| 25 | (Ib)FeCl$_2$$^b$ | 25 | 6.77 | 10,900 | MI < 0.01; M$_n$($^1$H):41,800 | 1.2 |
| 26 | (Ib)FeCl$_2$$^c$ | 25 | 10.79 | 17,700 | MI < 0.01; M$_n$($^1$H):no olefins | 1.2 |
| 27 | (Ib)CoCl$_2$ | 25 | 0.024 | 37.6 | | |
| 28 | (Ib)CoCl$_2$$^a$ | 25 | 1.974 | 3,390 | MI < 0.01; M$_n$($^1$H):7,110 | 8.8 |
| 29 | (Id)FeCl$_2$ | 25 | 13.11 | 18,700 | MI < 0.01; M$_n$($^1$H):no olefins | 1.0 |
| 30 | (Id)CoCl$_2$ | 25 | 1.819 | 3,160 | MI < 0.01; M$_n$($^1$H):2,650 | 13.2 |
| 31 | (Ie)FeCl$_2$ | 25 | 3.161 | 5,400 | MI < 0.01; M$_n$($^1$H):23,300 | 1.2 |
| 32 | (Ie5)CoCl$_2$$^a$ | 25 | 0.363 | 2,430 | M$_n$($^1$H):4,770 | 14.6 |
| 33 | (IIIa)FeCl$_2$ | 25 | 0.293 | 491 | M$_n$($^1$H):2,770 | 11.8 |
| 34 | (IIIa)CoCl$_2$ | 25 | 0.223 | 376 | M$_n$($^1$H):6,560 | 4.8 |

$^a$0.0053 mmol of cmpd were used.
$^b$Tolulene-insoluble fraction.
$^c$Toluene-soluble fraction.

TABLE 3

Ethylene Polymerization
(1.0 MPa, 1,2,4-Trichlorobenzene (8 mL), 0.02 mmol Cmpd, 18 h, 2 mL MMAO)

| Ex. | Cmpd | Temp (° C.) | PE(g) | PE(TO) | M.W. (MI, GPC, and/or $^1$H NMR) | Total Me |
|---|---|---|---|---|---|---|
| 35 | (Ia)FeCl$_2$ | 25 | 3.248 | 5,460 | MI < 0.01; M$_n$($^1$H):25,600 | 1.5 |
| 36 | (Ia)FeCl$_2$ | 60 | 0.666 | 1,140 | MI < 0.01; M$_n$($^1$H):14,100 | 2.2 |
| 37 | (Ia)CoCl$_2$ | 25 | 0.035 | 60.0 | | |
| 38 | (Ia)CoCl$_2$ | 60 | 0.040 | 60.9 | | |
| 39 | (Ib)FeCl$_2$$^a$ | 25 | 3.21 | 5,580 | MI < 0.01; M$_n$($^1$H):14,000 | 2.7 |
| 40 | (Ib)FeCl$_2$$^a$ | 60 | 0.742 | 1,290 | MI < 0.01; M$_n$($^1$H):8,200 | 2.8 |
| 41 | (Id)FeCl$_2$ | 25 | 4.359 | 7,390 | MI < 0.01; M$_n$($^1$H):33,500 | 1.7 |
| 42 | (Id)FeCl$_2$ | 60 | 1.174 | 2,000 | MI < 0.01; M$_n$($^1$H):24,400 | 2.1 |
| 43 | (Id)CoCl$_2$ | 25 | 0.834 | 1,420 | MI < 0.01; M$_n$($^1$H):4,840 | 12.0 |
| 44 | (Id)CoCl$_2$ | 60 | 0.398 | 672 | M$_n$($^1$H):3,590 | 11.2 |

$^a$Toluene-soluble fraction.

TABLE 4

Ethylene/1-Hexene (1-H) Copolymerization
(1.0 MPa, 1,2,4-Trichlorobenzene (TCB), 0.02 mmol Cmpd, 18 h, 25° C., 2 mL MMAO)

| Ex. | Cmpd | TCB (mL) | 1-H (mL) | Polymer (g) |
|---|---|---|---|---|
| 45 | (Ia)FeCl$_2$ | 4 | 4 | 0.758 |
| 46 | (Ib)FeCl$_2$$^a$ | 4 | 4 | 0.620 |
| 47 | (Id)CoCl$_2$$^a$ | 4 | 4 | 0.289 |
| 48 | (Id)FeCl$_2$ | 4 | 4 | 0.846 |
| 49 | (Id)FeCl$_2$ | 7 | 1 | 1.134 |
| 50 | (Id)FeCl$_2$ | 0 | 8 | 0.581 |

$^a$Toluene-soluble fraction.

What is claimed is:

1. A compound of the formula

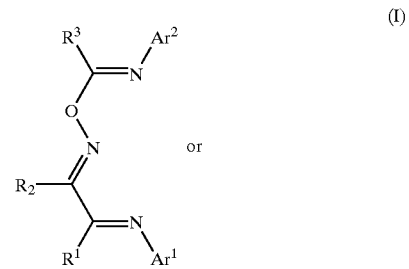

(I)

(III)

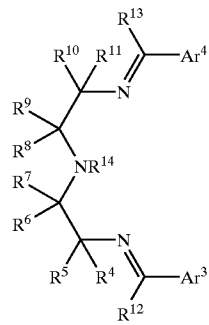

wherein:
  $R^1$, $R^2$ and $R^3$ are each independently hydrogen, hydrocarbyl, substituted hydrocarbyl or a functional group, or $R^1$ and $R^2$ taken together may form a ring;
  $Ar^1$ and $Ar^2$ are each independently aryl or substituted aryl;
  $R^4$, $R^5$, $R^6$, $R^7$, $R^8$, $R^9$, $R^{10}$, $R^{11}$, $R^{12}$ and $R^{13}$ are each independently hydrogen, hydrocarbyl, substituted hydrocarbyl, or a functional group, provided that any two of $R^4$, $R^5$, $R^6$, $R^7$, $R^8$, $R^9$, $R^{10}$ and $R^{11}$ that are vicinal to one another may form a ring;
  $R^{14}$ is hydrogen, hydrocarbyl or substituted hydrocarbyl; and
  $Ar^3$ and $Ar^4$ are each independently aryl or substituted aryl, and provided that when both $Ar^3$ and $Ar^4$ are phenyl rings $Ar^3$ and $Ar^4$ are each independently substituted in the 2 position or 2 and 6 position of their respective phenyl rings with optional substitution at any other position of said phenyl rings.

2. A compound of the formula (II)

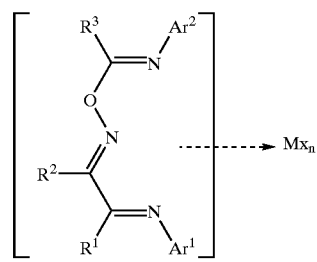

(IV)

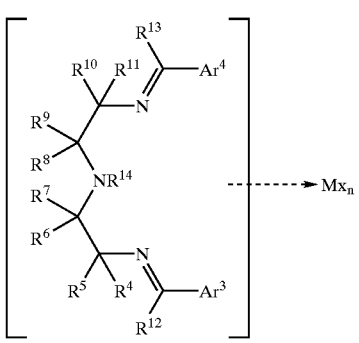

(V)

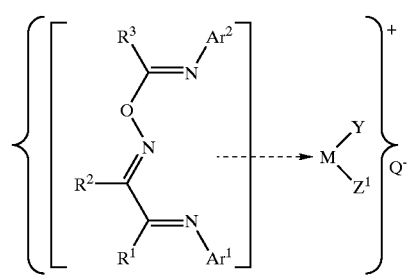

(VI)

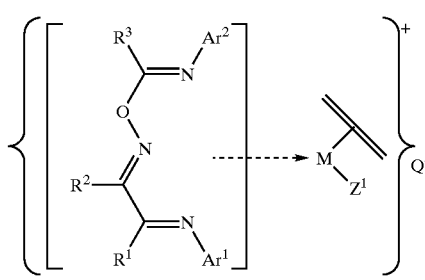

(VII)

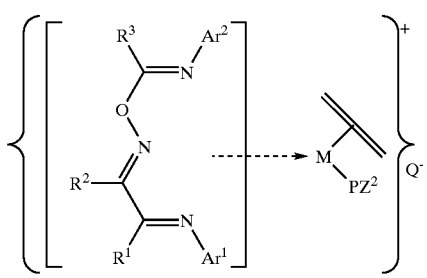

(VIII)

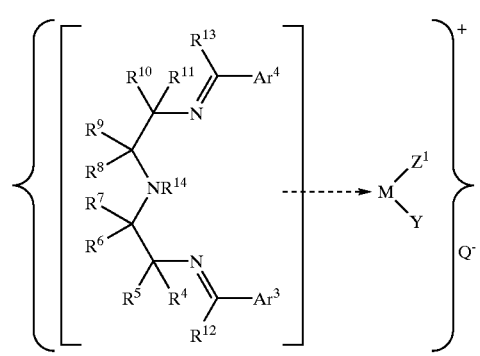

(IX)

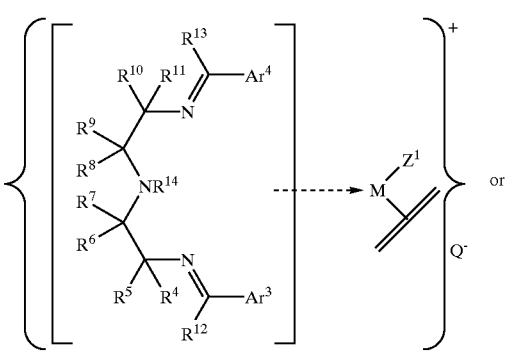 or

-continued

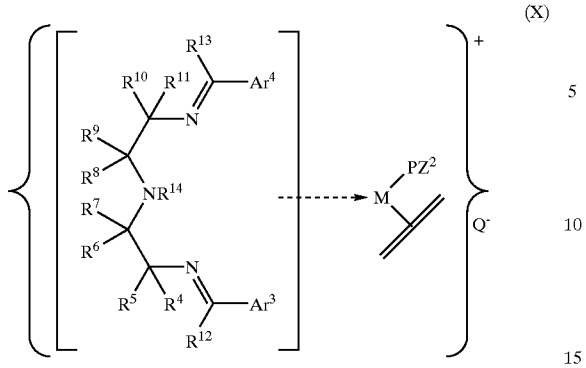 (X)

wherein:

M is Fe or Co;

$R^1$, $R^2$ and $R^3$ are each independently hydrogen, hydrocarbyl, substituted hydrocarbyl or a functional group, or $R^1$ and $R^2$ taken together may form a ring;

$Ar^1$ and $Ar^2$ are each independently aryl or substituted aryl;

$R^4$, $R^5$, $R^6$, $R^7$, $R^8$, $R^9$, $R^{10}$, $R^{11}$, $R^{12}$ and $R^{13}$ are each independently hydrogen, hydrocarbyl, substituted hydrocarbyl, or a functional group, provided that any two of $R^4$, $R^5$, $R^6$, $R^7$, $R^8$, $R^9$, $R^{10}$ and $R^{11}$ that are vicinal to one another may form a ring;

$R^{14}$ is hydrogen, hydrocarbyl or substituted hydrocarbyl;

$Ar^3$ and $Ar^4$ are each independently aryl or substituted aryl;

$Z^1$ is hydride or alkyl or any other anionic ligand into which ethylene can insert;

Y is a neutral ligand capable of being displaced by ethylene, or a vacant coordination site;

Q is a relatively non-coordinating anion;

P is a divalent polyethylene group containing one or more ethylene units; and $Z^2$ is an end group.

3. The compound as recited in claim 2 which is (II) or (IV).

4. The compound as recited in claim 1 or 3 wherein:

$R^1$ and $R^2$ are each independently hydrogen or alkyl containing 1 to 4 carbon atoms or $R^1$ and $R^2$ taken together are

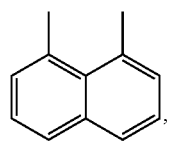,

-continued

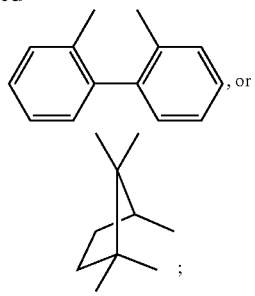, or $R^3$ is aryl, substituted aryl or alkyl;

$Ar^1$ and $Ar^2$ are 2-substituted with no substitution in the 6 position or 2,6-disubstituted phenyl, both with substitution optional at any other ring position;

$R^4$, $R^5$, $R^6$, $R^7$, $R^8$, $R^9$, $R^{10}$, $R^{11}$, $R^{12}$ and $R^{13}$ are each hydrogen;

$R^{14}$ is hydrogen or hydrocarbyl and $Ar^3$ and $Ar^4$ are 9-anthracenyl.

5. The compound as recited in claim 4 wherein:

both $R^1$ and $R^2$ are hydrogen or methyl;

$R^3$ is aryl, substituted aryl or alkyl containing 1 to 4 carbon atoms; and $R^1$ is methyl or hydrogen.

6. The compound as recited in claim 1 or 3 wherein:

(a) $Ar^1$ and $Ar^2$ are 2,6-diisopropylphenyl;
$R^1$ and $R^2$ are methyl; and
$R^3$ is phenyl; or (b) $Ar^1$ is 2,6-diisopropylphenyl;
$Ar^2$ is 2,6-dimethylphenyl;
$R^1$ and $R^2$ are methyl; and
$R^3$ is phenyl; or (c) $Ar^1$ and $Ar^2$ are 2,6-diisopropylphenyl;
$R^1$ and $R^2$ are methyl; and
$R^3$ is methyl; or (d) $Ar^1$ is 2,6-diisopropylphenyl;
$Ar^2$ is 2,6-dimethylphenyl;
$R^1$ and $R^2$ are methyl; and
$R^3$ is methyl; or (e) $Ar^1$ is 2,6-diisopropylphenyl;
$Ar^2$ is 2-methylphenyl;
$R^1$ and $R^2$ are methyl; and
$R^3$ is t-butyl; or (f) $R^4$, $R^5$, $R^6$, $R^7$, $R^8$, $R^9$, $R^{10}$, $R^{11}$, $R^{12}$, $R^{13}$ and $R^{14}$ are hydrogen; and
$Ar^3$ and $Ar^4$ are 9-anthracenyl.

\* \* \* \* \*